United States Patent
Starke et al.

(10) Patent No.: US 7,125,864 B2
(45) Date of Patent: Oct. 24, 2006

(54) BENZOTHIAZEPINE DERIVATIVES FOR THE TREATMENT OF HYPERLIPIDEMIA

(75) Inventors: Ingemar Starke, Molndal (SE); Mikael Ulf Johan Dahlstrom, Molndal (SE); David Blomberg, Molndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/489,009

(22) PCT Filed: Sep. 5, 2002

(86) PCT No.: PCT/GB02/04043

§ 371 (c)(1),
(2), (4) Date: Oct. 8, 2004

(87) PCT Pub. No.: WO03/022825

PCT Pub. Date: Mar. 20, 2003

(65) Prior Publication Data

US 2005/0032776 A1 Feb. 10, 2005

(30) Foreign Application Priority Data

Sep. 7, 2001 (GB) .................. 0121621.7

(51) Int. Cl.
- C07D 281/10 (2006.01)
- A61P 31/554 (2006.01)
- A61K 3/06 (2006.01)

(52) U.S. Cl. .................. 514/211.09; 540/552
(58) Field of Classification Search ................ 540/552; 514/211.09
See application file for complete search history.

(56) References Cited

U.S. PATENT DOCUMENTS

2002/0142054 A1  10/2002  Marlett et al.

FOREIGN PATENT DOCUMENTS

| DE | 19825804 | 12/1999 |
|---|---|---|
| EP | 0372542 A | 6/1990 |
| EP | 0 864 582 | 9/1998 |
| GB | 2262888 | 7/1993 |
| WO | 93/16055 | 8/1993 |
| WO | 94/18183 | 8/1994 |
| WO | 94/18184 | 8/1994 |
| WO | 96/05188 A | 2/1996 |
| WO | 96/08484 | 3/1996 |
| WO | 96/16051 | 5/1996 |
| WO | 97/33882 | 9/1997 |
| WO | 98/38182 | 9/1998 |
| WO | 98/40375 | 9/1998 |
| WO | 99/01149 | 1/1999 |
| WO | 99/32478 | 7/1999 |
| WO | 99/35135 A | 7/1999 |
| WO | 99/64409 | 12/1999 |
| WO | 99/64410 | 12/1999 |
| WO | 00/01687 | 1/2000 |
| WO | 00/38725 | 7/2000 |
| WO | 00/38726 | 7/2000 |
| WO | 00/38727 | 7/2000 |
| WO | 00/38728 | 7/2000 |
| WO | 00/38729 | 7/2000 |
| WO | 00/47568 | 8/2000 |
| WO | 00/61568 | 10/2000 |
| WO | 00/62810 | 10/2000 |
| WO | 01/60807 A1 | 8/2001 |
| WO | 01/66533 A | 9/2001 |
| WO | 01/68096 A2 | 9/2001 |
| WO | 01/68637 A2 | 9/2001 |
| WO | 02/08211 A2 | 1/2002 |
| WO | 02/32428 A2 | 4/2002 |
| WO | 02/50051 A1 | 6/2002 |
| WO | 02/053548 A1 | 7/2002 |
| WO | 03/020710 A1 | 3/2003 |
| WO | 03/022286 A1 | 3/2003 |
| WO | 03/022830 A1 | 3/2003 |
| WO | 03/061663 A1 | 7/2003 |
| WO | 03/091232 A2 | 11/2003 |
| WO | 03/106482 A2 | 12/2003 |
| WO | 2004/006899 A1 | 1/2004 |

(Continued)

OTHER PUBLICATIONS

Govers et al., Journal of Lipid Research, 35(5), 1994, pp. 741-748.

(Continued)

*Primary Examiner*—Bruck Kifle
(74) *Attorney, Agent, or Firm*—Morgan Lewis & Bockius LLP

(57) ABSTRACT

The present invention relates to compounds of formula (I): wherein variable groups are as defined within; pharmaceutically acceptable salts, solvates, solvates of such salts and prodrugs thereof and their use as ileal bile acid transport (IBAT) inhibitors for the treatment of hyperlipidemia. Processes for their manufacture and pharmaceutical compositions containing them are also described

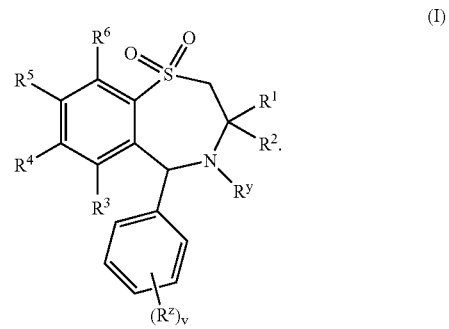

11 Claims, No Drawings

FOREIGN PATENT DOCUMENTS

WO    2004/076430 A1    9/2004
WO    2004/089350 A1    10/2004

OTHER PUBLICATIONS

Higaki et al., Arteriosclerosis, Thrombosis, and Vascular Biology, 18(8), 1998, pp. 1304-1311.

Ishibashi et al., Journal of Clinical Investigation, 92(2), 1993, pp. 883-893.

Lewis et al., Journal of Lipid Research, 36, 1995, pp. 1098-1105.

Plump et al., Cell, (71), 1992, pp. 343-353.

Schiller, Alimentary Pharmacology and Therapeutics, 15(6), 2001, pp. 749-763.

Sprong et al., J. Nutrition (US), 132(6), 2002, pp. 1269-1274.

Van'Tilburg et al., Gastroenterology, 98(1), 1989, pp. 25-32.

Welberg et al., Scandinavian J. Gastroenterology Suppl Norway, 188, 1991, pp. 52-59.

BENZOTHIAZEPINE DERIVATIVES FOR THE TREATMENT OF HYPERLIPIDEMIA

This application is a national stage filing under 35 U.S.C. 371 of International Application No. PCT/GB02/04043, filed Sep. 5, 2002, which claims priority from GB Application No. GB 0121621.7, filed Sep. 7, 2001, the specification of each of which are incorporated by reference herein. International Application No. PCT/ GB02/04043 was published under PCT Article 21(2) in English.

This invention relates to benzothiazepine derivatives, or pharmaceutically acceptable salts, solvates, solvates of such salts and prodrugs thereof These benzothiazepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiazepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930–1938 and "Diabetes and Cardiovascular Disease: A Statement for Healthcare Professionals from the American Heart Association" Grundy S, Benjamin I., Burke G., et al; Circulation, 1999, 100, 1134–46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269–74) involved the treatment with substances with an IBAT inhibitory effect.

Re-absorption of bile acid from the gastro-intestinal tract is a normal physiological process which mainly takes place in the ileum by the IBAT mechanism. Inhibitors of IBAT can be used in the treatment of hypercholesterolaemia (see for instance "Interaction of bile acids and cholesterol with nonsystemic agents having hypocholesterolaemic properties", Biochemica et Biophysica Acta, 1210 (1994) 255–287). Thus, suitable compounds having such inhibitory IBAT activity are also useful in the treatment of hyperlipidaemic conditions. Compounds possessing such IBAT inhibitory activity have been described, see for instance the compounds described in WO 93/16055, WO 94/18183, WO 94/18184, WO 96/05188, WO 96/08484, WO 96/16051, WO 97/33882, WO 98/38182, WO 99/35135, WO 98/40375, WO 99/35153, WO 99/64409, WO 99/64410, WO 00/01687, WO 00/47568, WO 00/61568, WO 01/68906, DE 19825804, WO 00/38725, WO 00/38726, WO 00/38727, WO 00/38728, WO 00/38729, WO 01/68906, WO 01/66533, WO 02/50051 and EP 0 864 582.

A further aspect of this invention relates to the use of the compounds of the invention in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In addition, these compounds are expected to be useful for the prevention and treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks.

The present invention is based on the discovery that certain benzothiazepine compounds surprisingly inhibit IBAT. Such properties are expected to be of value in the treatment of disease states associated with hyperlipidaemic conditions.

Accordingly, the present invention provides a compound of formula (I):

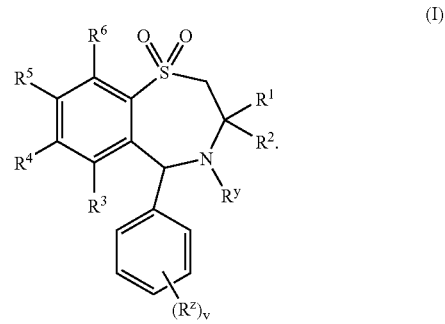

(I)

wherein:

One of $R^1$ and $R^2$ are selected from hydrogen $C_{1-6}$alkyl or $C_{2-6}$alkenyl and the other is selected from $C_{1-6}$alkyl or $C_{2-6}$alkenyl;

$R^y$ is selected from hydrogen, hydroxy, $C_{1-6}$alkyl, $C_{1-4}$alkoxy and $C_{1-6}$alkanoyloxy;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

v is 0–5;

one of R⁴ and R⁵ is a group of formula (IA):

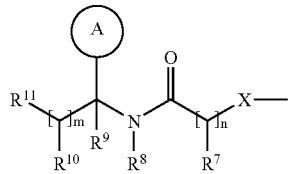
(IA)

R³ and R⁶ and the other of R⁴ and R⁵ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulphamoyl; wherein R³ and R⁶ and the other of R⁴ and R⁵ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

R⁷ is hydrogen, $C_{1-4}$alkyl, carbocyclyl or heterocyclyl; wherein R⁷ is optionally substituted by one or more substituents selected from $R^{18}$;

R⁸ is hydrogen or $C_{1-4}$alkyl;

R⁹ is hydrogen or $C_{1-4}$alkyl;

R¹⁰ is hydrogen, $C_{1-4}$alkyl, carbocyclyl or heterocyclyl; wherein R¹⁰ is optionally substituted by one or more substituents selected from $R^{19}$;

R¹¹ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or R¹¹ is a group of formula (IB):

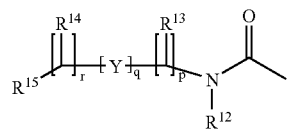
(IB)

wherein:

Y is —N(R$^x$)—, —N(R$^x$)C(O)—, —O—, and —S(O)a—; wherein a is 0–2 and R$^x$ is hydrogen or $C_{1-4}$alkyl;

R¹² is hydrogen or $C_{1-4}$alkyl;

R¹³ and R¹⁴ are independently selected from hydrogen, $C_{1-6}$alkyl, carbocyclyl or heterocyclyl; wherein R¹³ and R¹⁴ may be independently optionally substituted by one or more substituents selected from $R^{20}$;

R¹⁵ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$alkyl; or R¹⁵ is a group of formula (IC):

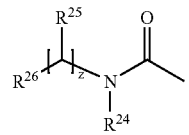
(IC)

wherein:

R²⁴ is selected from hydrogen or $C_{1-4}$alkyl;

R²⁵ is selected from hydrogen, $C_{1-4}$alkyl, carbocyclyl, heterocyclyl or $R^{27}$; wherein said $C_{1-4}$alkyl, carbocyclyl or heterocyclyl may be independently optionally substituted by one or more substituents selected from $R^{28}$;

R²⁶ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from $C_{1-6}$alkyl;

p is 1–3; wherein the values of R¹³ may be the same or different;

q is 0–1;

r is 0–3; wherein the values of R¹⁴ may be the same or different;

m is 0–2; wherein the values of R¹⁰ may be the same or different;

n is 1–3; wherein the values of R⁷ may be the same or different;

z is 0–3; wherein the values of R²⁵ may be the same or different;

R¹⁶, R¹⁷ and R¹⁸ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)₂sulphamoyl; wherein R¹⁶, R¹⁷ and R¹⁸ may be independently optionally substituted on carbon by one or more $R^{21}$;

R¹⁹, R²⁰, R²⁷ and R²⁸ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)₂amino, $C_{1-4}$alkanoylamino, N—($C_{1-4}$alkyl)carbamoyl, N,N—($C_{1-4}$alkyl)₂carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)₂sulphamoyl, carbocyclyl, heterocyclyl, sulpho, sulphino, amidino, ($C_{1-4}$alkyl)₃silyl, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein R¹⁹ and R²⁰ may be independently optionally substituted on carbon by one or more $R^{22}$;

R²¹ and R²² are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

According to a further feature of the present invention there is provided a compound of formula (I):

(I)

wherein:
One of $R^1$ and $R^2$ are selected from hydrogen or $C_{1-6}$alkyl and the other is selected from $C_{1-6}$alkyl;

$R^y$ is selected from hydrogen, hydroxy, $C_{1-6}$alkyl, $C_{1-4}$alkoxy and $C_{1-6}$alkanoyloxy, $R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

v is 0–5;

one of $R^4$ and $R^5$ is a group of formula (IA):

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted by one or more substituents selected from $R^{17}$;

$R^7$ is hydrogen, $C_{1-4}$alkly, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein $R^c$ and $R^d$ are independently selected from $C_{1-6}$alkyl; or $R^{11}$ is a group of formula (IB):

(IB)

wherein:
Y is —N($R^x$)—, —N($R^x$)C(O)—, —O—, and —S(O)a—; wherein a is 0–2 and $R^x$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from $C_{1-6}$alkyl p is 1–3; wherein the values of $R^{13}$ may be the same or different;

q is 0–1;

r is 0–3; wherein the values of $R^{14}$ may be the same or different;

m is 0–2; wherein the values of $R^{10}$ may be the same or different;

n is 1–3; wherein the values of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{16}$, $R^{17}$ and $R^{18}$ may be independently optionally substituted on carbon by one or more $R^{21}$;

$R^{19}$ and $R^{20}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein $R^a$ and $R^b$ are independently selected from $C_{1-6}$alkyl; wherein $R^{19}$ and $R^{20}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, alkyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-6}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3–12 atoms of which at least one atom is chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. Examples and suitable values of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl.

"Aryl" is a totally unsaturated, mono or bicyclic carbon ring that contains 3–12 atoms. Preferably "aryl" is a monocyclic ring containing 5 or 6 atoms or a bicyclic ring containing 9 or 10 atoms. Suitable values for "aryl" include phenyl or naphthyl. Particularly "aryl" is phenyl.

A "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3–12 atoms; wherein a —$CH_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$alkanoyloxy" and "$C_{1-4}$alkanoyloxy" is acetoxy. Examples of "$C_{1-6}$alkoxycarbonyl" and "$C_{1-4}$alkoxycarbonyl" include methoxycarbonyl, ethoxycarbonyl, n- and t-butoxycarbonyl. Examples of "$C_{1-4}$alkoxy" "$C_{1-4}$alkoxy" include methoxy, ethoxy and propoxy. Examples of "$C_{1-6}$alkanoylamino" and "$C_{1-4}$alkanoylamino" include formamido, acetamido and propionylamino. Examples of "$C_{1-6}$alkylS(O)$_a$ wherein a is 0 to 2" and "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl" and "$C_{1-4}$alkanoyl" include propionyl and acetyl. Examples of "N—($C_{1-6}$alkyl)amino" and "N—($C_{1-4}$alkyl)amino" include methylamino and ethylamino. Examples of "N,N—($C_{1-6}$alkyl)$_2$amino" and "N,N—($C_{1-4}$alkyl)$_2$amino" include di-N-methylamino, di-(N-ethyl)amino and N-ethyl-N-methylamino. Examples of "$C_{2-6}$alkenyl" and "$C_{2-4}$alkenyl" are vinyl, allyl and 1-propenyl. Examples of "$C_{2-6}$alkynyl" and "$C_{2-4}$alkynyl" are ethynyl, 1-propynyl and 2-propynyl. Examples of "N—($C_{1-6}$alkyl)sulphamoyl" and "N—($C_{1-4}$alkyl)sulphamoyl" are N-(methyl)sulphamoyl and N-(ethyl)sulphamoyl. Examples of "N—($C_{1-6}$alkyl)$_2$sulphamoyl" and "N—($C_{1-4}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" and "N—($C_{1-4}$alkyl)carbamoyl" are methylaminocarbonyl and ethylaminocarbonyl. Examples of "N,N—($C_{1-6}$alkyl)$_2$carbamoyl" and "N,N—($C_{1-4}$alkyl)$_2$carbamoyl" are dimethylaminocarbonyl and methylethylaminocarbonyl. Examples of "($C_{1-4}$alkyl)$_3$silyl," include trimethylsilyl and methyldiethylsilyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I).

examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Particular values are as follows. Such values maybe used where appropriate with any of the definitions, claims or embodiments defined hereinbefore or hereinafter.

$R^1$ and $R^2$ are $C_{1-4}$alkyl.
$R^1$ and $R^2$ are butyl.
One of $R^1$ and $R^2$ is ethyl and the other is butyl.
One of $R^1$ and $R^2$ is ethyl and the other is butyl or $R^1$ and $R^2$ are both butyl.
v is 0 or 1.
v is 0.
$R^z$ is $C_{1-4}$alkyl.
$R^y$ is hydrogen.
$R^y$ is hydrogen or hydroxy.
$R^3$ and $R^6$ are hydrogen.
$R^4$ is methylthio.
$R^4$ is hydrogen.
$R^4$ is hydrogen, halo or $C_{1-4}$alkylS(O)$_a$ wherein a is 0.
$R^4$ is hydrogen, bromo or methylthio.
$R^5$ is a group of formula (IA) (as depicted above) wherein:
X is —O—;
n is 1;
$R^7$ is hydrogen;
$R^8$ is hydrogen;
$R^9$ is hydrogen;
m is 0; and
$R^{11}$ is carboxy.
$R^5$ is N-((R)-α-carboxybenzyl)carbamoylmethoxy.
$R^5$ is a group of formula (IA) (as depicted above); wherein
X is —O—;
Ring A is aryl; wherein Ring A is optionally substituted by one or more substituents selected from $R^{17}$;
$R^7$ is hydrogen;
$R^8$ is hydrogen;
$R^9$ is hydrogen;
$R^{11}$ is carboxy; or $R^{11}$ is a group of formula (IB) (as depicted above); wherein:
$R^{12}$ is hydrogen;
$R^{13}$ is hydrogen;
$R^{15}$ is carboxy or sulpho;
p is 1 or 2;
q is 0;
r is 0;
m is 0;
n is 1; and
$R^{17}$ is hydroxy.
$R^5$ is a group of formula (IA) (as depicted above); wherein
X is —O—;
Ring A is phenyl or 4-hydroxyphenyl;
$R^7$ is hydrogen;
$R^8$ is hydrogen;
$R^9$ is hydrogen;
$R^{11}$ is carboxy; or $R^{11}$ is a group of formula (IB) (as depicted above); wherein:
$R^{12}$ is hydrogen;
$R^{13}$ is hydrogen;
$R^{15}$ is carboxy or sulpho;
p is 1 or 2;
q is 0;
r is 0;
m is 0; and
n is 1;
$R^5$ is N-((R)-α-carboxybenzyl)carbamoylmethoxy, N-{(R)-α-[N-(carboxymethyl)carbamoyl]benzyl}carbamoylmethoxy; or N-{(R)-α-[N-(2-sulphoethyl)carbamoyl]4-hydroxybenzyl}carbamoylmethoxy.

Therefore in one aspect of the invention there is provided a compound of formula (I) (as depicted above)
$R^1$ and $R^2$ are $C_{1-4}$alkyl;
v is 0;
$R^y$ is hydrogen or hydroxy;
$R^3$ and $R^6$ are hydrogen;
$R^4$ is hydrogen, halo or $C_{1-4}$alkylS(O)$_a$ wherein a is 0;
$R^5$ is a group of formula (IA) (as depicted above); wherein
X is —O—;
Ring A is aryl; wherein Ring A is optionally substituted by one or more substituents selected from $R^{17}$;
$R^7$ is hydrogen;
$R^8$ is hydrogen;
$R^9$ is hydrogen;

$R^{11}$ is carboxy; or $R^{11}$ is a group of formula (IB) (as depicted above); wherein:

$R^{12}$ is hydrogen;

$R^{13}$ is hydrogen;

$R^{15}$ is carboxy or sulpho;

p is 1 or 2;

q is 0;

r is 0;

m is 0;

n is 1; and $R^{17}$ is hydroxy;

or a pharmaceutically acceptable salt, solvate, solvate of such a salt or a prodrug thereof.

Therefore in one aspect of the invention there is provided a compound of formula (I) (as depicted above)

One of $R^1$ and $R^2$ is ethyl and the other is butyl;

v is 0;

$R^y$ is hydrogen or hydroxy;

$R^3$ and $R^6$ are hydrogen;

$R^4$ is hydrogen, bromo or methylthio;

$R^5$ is N-((R)-α-carboxybenzyl)carbamoylmethoxy; N-{(R)-α-[N-(carboxymethyl)carbamoyl]benzyl}carbamoylmethoxy; or N-{(R)-α-[N-(2-sulphoethyl)carbamoyl]4-hydroxybenzyl}carbamoylmethoxy;

or a pharmaceutically acceptable salt, solvate, solvate of such a salt or a prodrug thereof.

In another aspect of the invention, preferred compounds of the invention are any one of the examples or a pharmaceutically acceptable salt, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1): oxidising a benzothiazepine of formula (II):

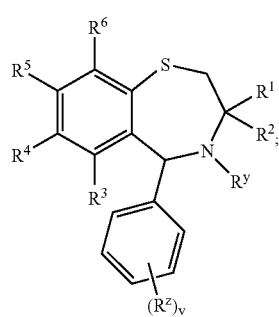

(II)

Process 2): for compounds of formula (I) wherein X is —O—, —NR$^a$ or —S—; reacting a compound of formula (IIIa) or (IIIb):

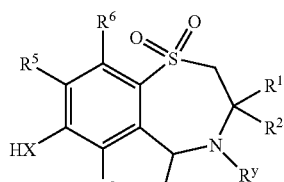

(IIIa)

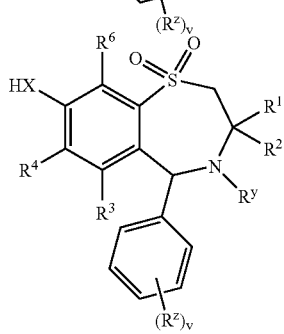

(IIIb)

with a compound of formula (IV):

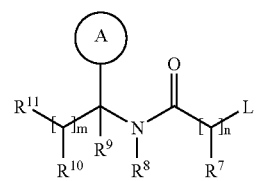

(IV)

wherein L is a displaceable group;

Process 3): reacting an acid of formula (Va) or (Vb):

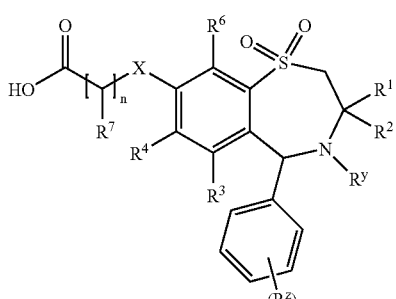

(Va)

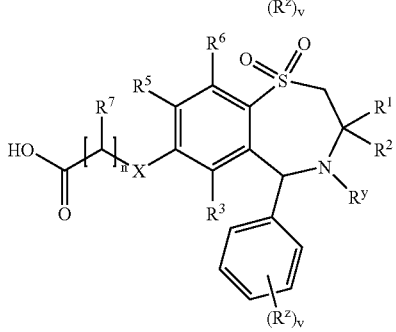

(Vb)

or an activated derivative thereof; with an amine of formula (VI):

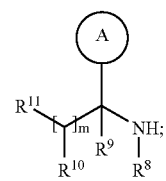
(VI)

Process 4): for compounds of formula (I) wherein $R^{11}$ is a group of formula (IB); reacting a compound of formula (I) wherein $R^{11}$ is carboxy with an amine of formula (VII):

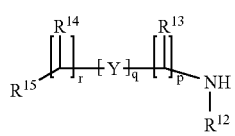
(VII)

Process 5): for compounds of formula (I) wherein $R^{11}$ is a group of formula (IB) and $R^{15}$ is a group of formula (IC) reacting a compound of formula (I) wherein $R^{15}$ is carboxy with an amine of formula (VIII):

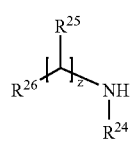
(VIII)

Process 6) for compounds of formula (I) wherein one of $R^4$ and $R^5$ are independently selected from $C_{1-6}$alkylthio optionally substituted on carbon by one or more $R^{16}$; reacting a compound of formula (IXa) or (IXb):

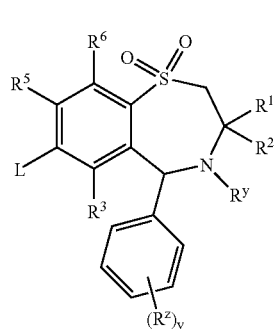
(IXa)

-continued

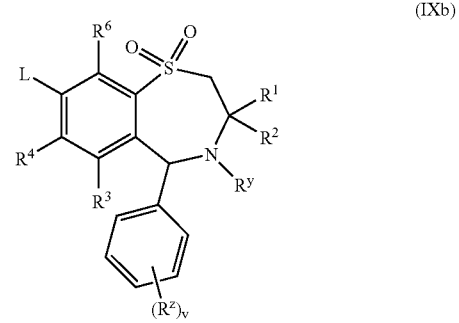
(IXb)

wherein L is a displaceable group; with a thiol of formula (X):

$$R^m\text{—H} \quad (X)$$

wherein $R^m$ is $C_{1-6}$alkylthio optionally substituted on carbon by one or more $R^{16}$;

Process 7): for compounds of formula (I) wherein $R^{11}$ is carboxy; deprotecting a compound of formula (XIa):

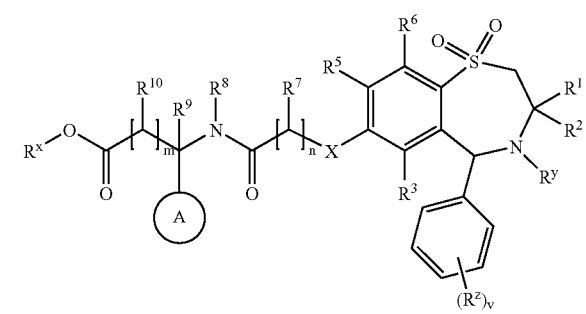
(XIa)

or (XIb):

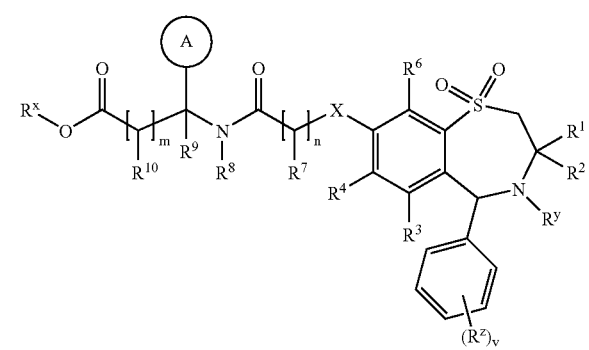
(XIb)

wherein $R^x$ together with the —OC(O)— group to which it is attached forms an ester;

Process 8): for compounds of formula (I) wherein $R^{11}$ is a group of formula (IB) and $R^{15}$ is carboxy; deprotecting a compound of formula (XIIa):

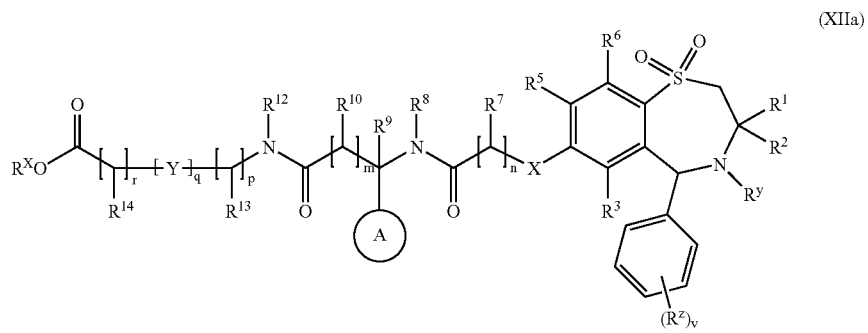

(XIIa)

or (XIIb):

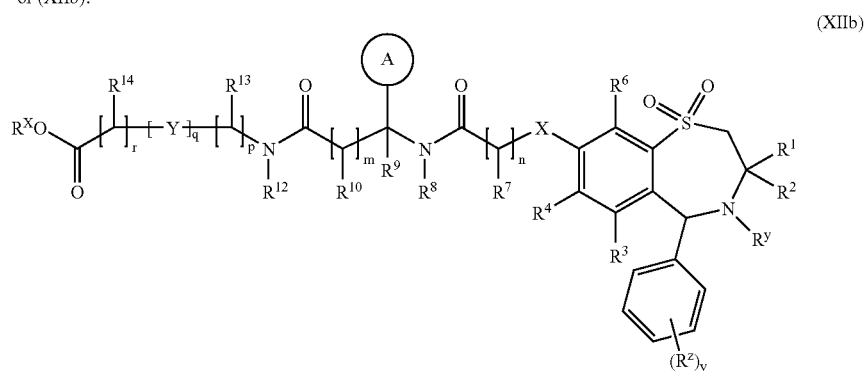

(XIIb)

wherein $R^x$ together with the —OC(O)— group to which it is attached forms an ester;

Process 9): for compounds of formula (I) wherein $R^{11}$ is a group of formula (IB) and Y is —N($R^x$)C(O)—; reacting an acid of formula (XIIIa):

(XIIIa)

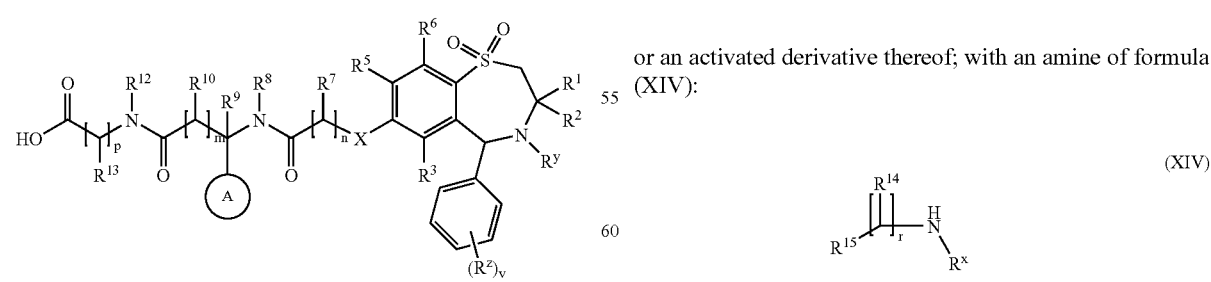

or (XIIIb):

(XIIIb)

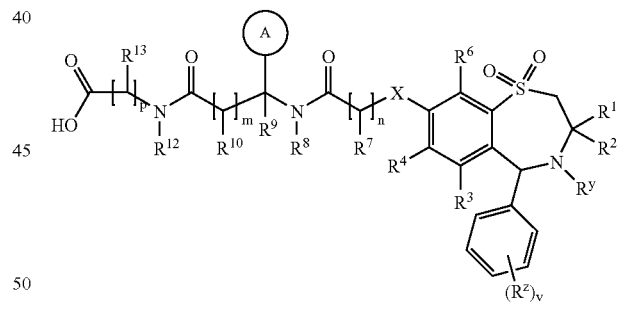

or an activated derivative thereof; with an amine of formula (XIV):

(XIV)

or Process 10): for compounds of formula (I) wherein $R^{11}$ is a group of formula (IB), $R^{15}$ is a group of formula (IC) and $R^{26}$ is carboxy, deprotecting a compound of formula (XVa):

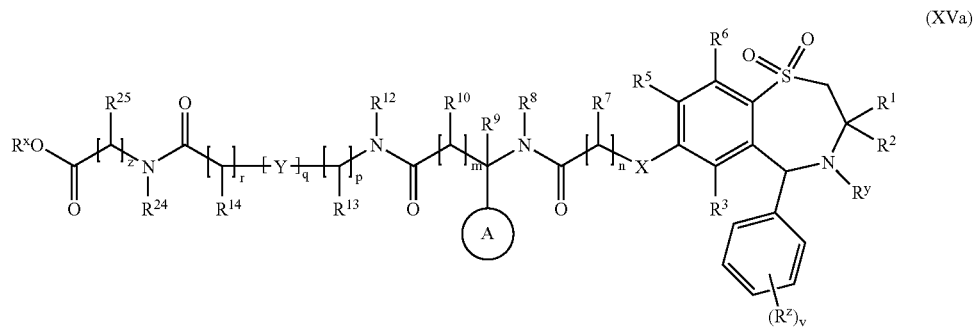

(XVa)

or (XVb):

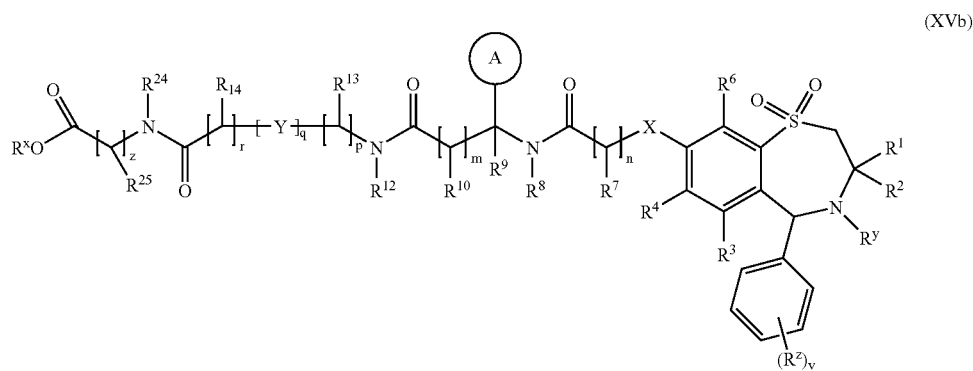

(XVb)

wherein $R^x$ together with the —OC(O)— group to which it is attached forms an ester; and thereafter if necessary or desirable:

i) converting a compound of the formula (I) into another compound of the formula (I);
ii) removing any protecting groups;
iii) forming a pharmaceutically acceptable salt, solvate, solvate of such a salt or a prodrug.

L is a displaceable group, suitable values for L are for example, a halogeno or sulphonyloxy group, for example a chloro, bromo, methanesulphonyloxy or toluene-4-sulphonyloxy group.

$R^x$ together with the —OC(O)— group to which it is attached forms an ester. Preferably $R^x$ is methyl or ethyl. More preferably $R^x$ is methyl. In another aspect of the invention $R^x$ is $C_{1-6}$alkyl or phenyl$C_{1-6}$alkyl, preferably $C_{1-4}$alkyl or benzyl, more preferably t-butyl, methyl, ethyl or benzyl.

Specific reaction conditions for the above reactions are as follows.

Process 1): Benzothiazepines of formula (II) may be oxidised under standard sulphur oxidation conditions; for example using hydrogen peroxide and trifluoroacetic acid at a temperature in the range of 0° C. to reflux, preferably at or near room temperature.

Compounds of formula (II) may be prepared according to Scheme I:

Scheme 1
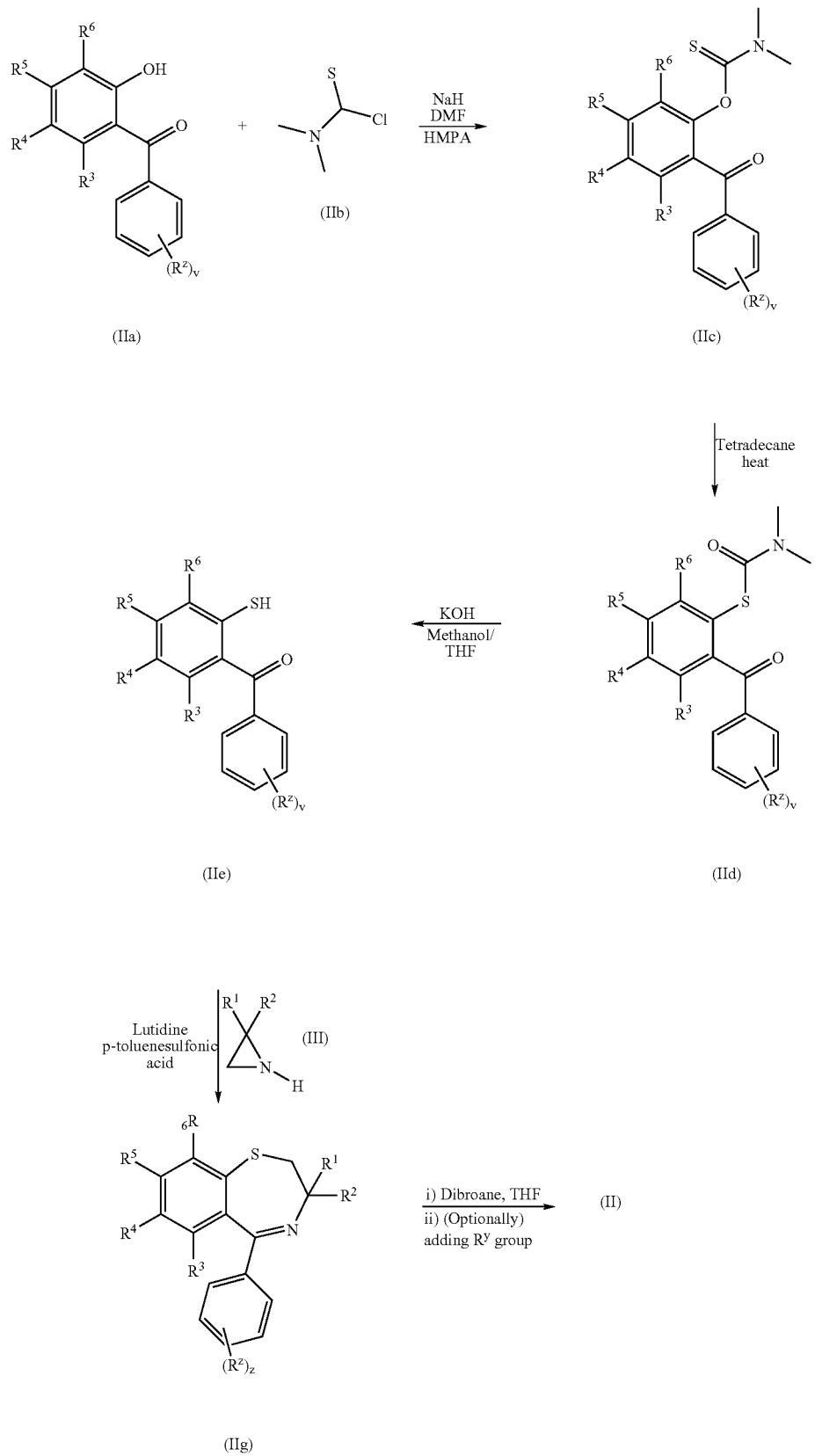

Compounds of formula (IIa), (IIb) and (IIf) are commercially available compounds, or they are known in the literature, or they are prepared by standard processes known in the art.

Process 2): Compounds of formula (IIIa) or (IIIb) may be reacted with compounds of formula (IV) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (IIIa) or (IIIb) may be prepared in a similar manner to compounds of formula (II) but wherein $R^4$ or $R^5$ is —OH, —NH($R^a$) or —SH (optionally for —SO— and —$SO_2$— followed by the oxidation step of Process 1). Compounds of formula (IIIa) or (IIIb) wherein X is —O— or —S— may also be prepared by the procedures disclosed in WO 9605188.

Compounds of formula (IV) are commercially available compounds, or they are known in the literature, or they are prepared by standard processes known in the art.

Process 3) and Process 4) and Process5) and Process 9):
Acids and amines may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of –40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of –40 to 40° C.

Compounds of formula (Va) or (Vb) wherein X=—O—,—$NR^a$,—S— may be prepared according to Scheme 2:

Scheme 2

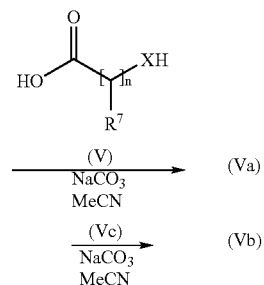

(IXa) $\xrightarrow[\text{MeCN}]{\text{(V)} \atop \text{NaCO}_3}$ (Va)

(IXb) $\xrightarrow[\text{MeCN}]{\text{(Vc)} \atop \text{NaCO}_3}$ (Vb)

Wherein L in (IXa) and (IXb) is a displaceable group e.g. bromo, chloro, fluoro, mesyl or tosyl and wherein X is —O—,—S—, $NR^a$ (optionally for —SO— and —$SO_2$— followed by the oxidation step of Process 1).

Compounds of formula (Va) and (Vb) where X is —SO— or —$SO_2$— may be prepared by oxidising the resulting compounds of formula (Va) and (Vb) from Scheme 2 where X is —S—.

Compounds of formula (Va) or (Vb) wherein X is —$CH_2$—, and n is 1, may be prepared according to Scheme 3.

Scheme 3

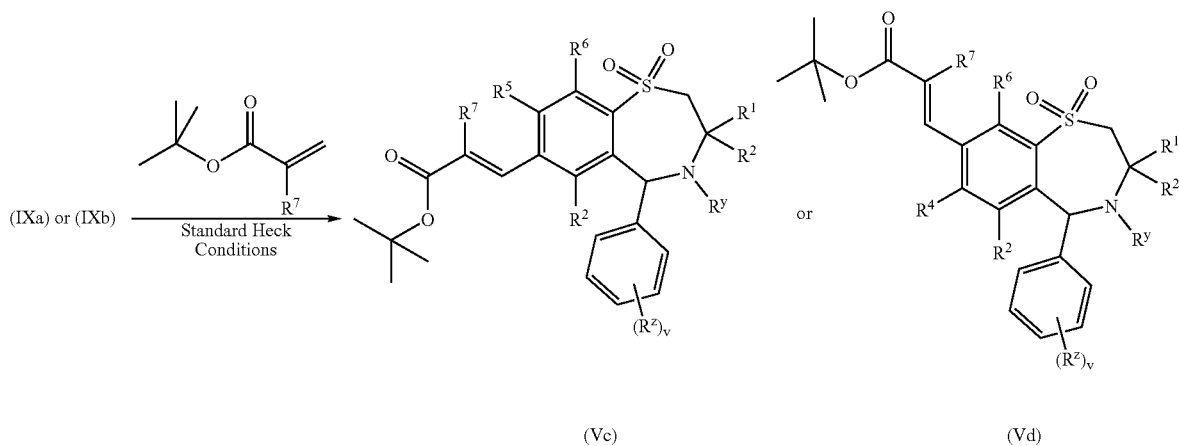

(Vc)    (Vd)

Hydrolysis

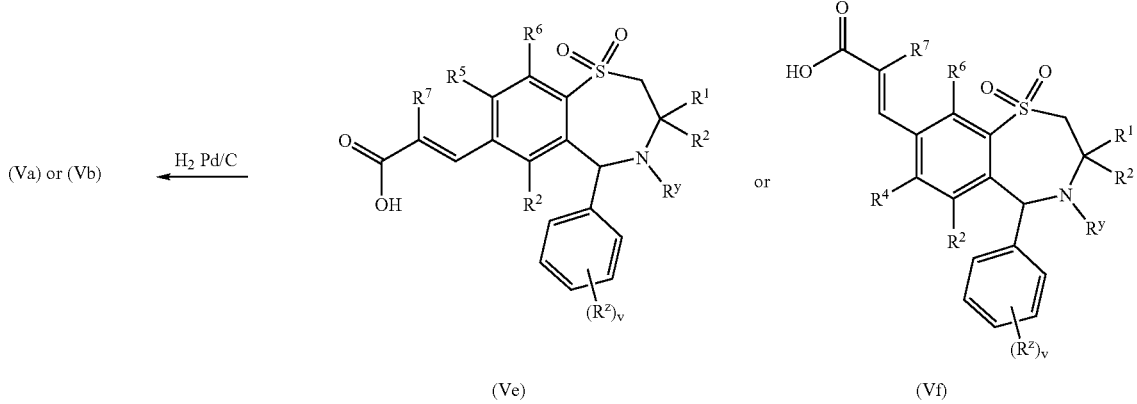

The skilled person will appreciate that the above reaction scheme may be manipulated to prepare compounds of formula (Va) or (Vb) where n is 2 or 3.

Compounds of formula (XIIIa) or (XIIIb) maybe prepared by manipulations known to the skilled person of the processes described herein.

Compounds of formula (Vc), (VI), (VII), (VIII) and (XIV) are commercially available compounds, or they are known in the literature, or they are prepared by standard processes known in the art.

Process 6): Compounds of formula (IXa) and (IXb) may be reacted with thiols of formula (X) in the presence of base, for example an inorganic base such as sodium carbonate or an organic base such as Hunigs base, in the presence of a suitable solvent such as DMF or THF at a temperature in the range of 0° C. to reflux.

Compounds of formula (IXa) and (IXb) may be prepared by any of the procedures above for the preparation of compounds of formula (I), but wherein one of $R^4$ and $R^5$ is L.

Compounds of formula (X) are commercially available compounds, or they are known in the literature, or they are prepared by standard processes known in the art.

Process 7) and Process 8) and Process 10): Esters of formula (XIa), (XIb), (XIIa), (XIIb), (XVa) and (XVb) may be deprotected under standard conditions such as those described below, for Example they may be deprotected with sodium hydroxide in methanol at room temperature.

Esters of formula (XIa), (XIb), (XIIa), (XIIb), (XVa) and (XVb) may be prepared by any of the procedures above for the preparation of compounds of formula (I), but wherein $R^{11}$ or $R^{15}$ or $R^{26}$ is an ester.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifuoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBAT-transfected cells (Smith L., Price-Jones M. J., Hugnes K. T. and Jones N. R. A.; J Biomolecular Screening, 3, 227–230) or in vivo by studying the effect on radiolabelled bile acid absorption in mice/rats (Lewis M. C., Brieaddy L. E. and Root C., J., J Lip Res 1995, 36, 1098–1105).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5–5000 mg per square meter body area of the animal, i.e. approximately 0.02–100 mg/kg, preferably 0.02–50 mg/kg, and this normally provides a therapeutically-effective dose. A unit dose form such as a tablet or capsule will usually contain, for example 1–250 mg of active ingredient. Preferably a daily dose in the range of 1–50 mg/kg, particularly 0.1–10 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore, in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore, in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

Herein, where "the production of an IBAT inhibitory effect" or "producing an IBAT inhibitory effect" is referred to particularly this refers to the treatment of hyperlipidaemic conditions. In another aspect, "the production of an IBAT inhibitory effect" or "producing an IBAT inhibitory effect" refers to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In another aspect "the production of an IBAT inhibitory effect" or "producing an IBAT inhibitory effect" refers to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks. In another aspect "the production of an IBAT inhibitory effect" or "producing an IBAT inhibitory effect" refers to the treatment of atherosclerosis, coronary heart diseases, myocardial infarction, angina pectoris, peripheral vascular diseases, stroke and transient ischaemic attacks in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 0.1–50 mg/kg preferably 0.1–10 mg/kg is envisaged.

The IBAT inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl(methylsulphonyl)amimo]pyrimidin-5-yl](3R, 5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl(methylsulphonyl)amino]pyrimidin-5-yl](3R,5S)-3,5-dihydroxyhept-6-enoic acid, or a pharmaceutically acceptable salt, solvate, solvate of such a salt or a prodrug thereof. A more particular statin is rosuvastatin calcium salt.

In an additional aspect of the invention, the compound of formula (I), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof and a bile acid binder.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) a bile acid binder; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form;
c) a bile acid binder; in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) a bile acid binder; in a third unit dosage form; and
d) container means for containing said first, second and third dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22–page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751–54, 1998 which are incorporated herein by reference;

a fibric acid derivative; for example clofibrate, gemfibrozil, fenofibrate, ciprofibrate and bezafibrate;

a nicotinic acid derivative, for example, nicotinic acid (niacin), acipimox and niceritrol;

a phytosterol compound for example stanols;

probucol;

an anti-obesity compound for example orlistat (EP 129, 748) and sibutramine (GB 2,184,122 and U.S. Pat. No. 4,929,629);

an antihypertensive compound for example an angiotensin converting enzyme inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, a diuretic or a vasodilator;

insulin;

sulphonylureas including glibenclamide, tolbutamide;

metformin; and/or acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula (I) include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perndopfril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623–634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041, NN622/Ragaglitazar, BMS 298585 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;
b) a PPAR alpha and/or gamma agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, a PPAR alpha and/or gamma agonist, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention. For Example compounds of formula (XIa), (XIb), (XIIa), (XIIb), (XVa) and (XVb) show IBAT inhibitory activity when tested in the above referenced in vitro test assay and are thus claimed as a further feature of the invention.

Thus in a further feature of the invention, there is provided a compound of formula (XIa), (XIb), (XIIa), (XIIb), (XVa) or (XVb), or a pharmaceutically acceptable salt, solvate, solvate of such a salt or a prodrug thereof.

Therefore according to a further aspect of the invention there is provided a pharmaceutical composition which comprises a compound of formula (XIa), (XIb), (XIIa), (XIIb), (XVa) or (XVb), or a pharmaceutically acceptable salt, solvate, solvate of such a salt or a prodrug thereof, as defined hereinbefore in association with a pharmaceutically-acceptable diluent or carrier.

According to an additional aspect of the present invention there is provided a compound of the formula (XIa), (XIb), (XIIa), (XIIb), (XVa) or (XVb), or a pharmaceutically acceptable salt, solvate, solvate of such a salt or a prodrug thereof, as defined hereinbefore for use in a method of prophylactic or therapeutic treatment of a warm-blooded animal, such as man.

Thus according to this aspect of the invention there is provided a compound of the formula (XIa), (XIb), (XIIa), (XIIb), (XVa) or (XVb), or a pharmaceutically acceptable salt, solvate, solvate of such a salt or a prodrug thereof, as defined hereinbefore for use as a medicament.

According to another feature of the invention there is provided the use of a compound of the formula (XIa), (XIb), (XIIa), (XIIb), (XVa) or (XVb), or a pharmaceutically acceptable salt, solvate, solvate of such a salt or a prodrug thereof as defined hereinbefore in the manufacture of a medicament for use in the production of an IBAT inhibitory effect in a warm-blooded animal, such as man.

According to another feature of the invention there is provided the use of a compound of the formula (XIa), (XIb), (XIIa), (XIIIb), (XVa) or (XVb), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (XIa), (XIb), (XIIa), (XIIb), (XVa) or XVb), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (XIa), (XIb), (XIIa), (XIIb), (XVa) or (XVb), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18–25° C., with solvents of HPLC grade under anhydrous conditions, unless otherwise stated;

(iii) column chromatography (by the flash procedure) was performed on Silica gel 40–63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CD_3OD$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer; and peak multiplicities are shown as follows: s, singlet; d, doublet; dd, double doublet; t, triplet; tt, triple triplet; q, quartet; tq, triple quartet; m, multiplet; br, broad; LCMS were recorded on a Waters ZMD, LC column xTerra MS $C_8$(Waters), detection with a HP 1100 MS-detector diode array equipped; mass spectra (MS) (loop) were recorded on VG Platform II (Fisons Instruments) with a HP-1100 MS-detector diode array equipped; unless otherwise stated the mass ion quoted is $(MH^+)$;

(vi) unless further details are specified in the text, analytical high performance liquid chromatography (HPLC) was performed on Prep LC 2000 (Waters), Kromasil $C_8$, 7 μm, (Akzo Nobel); MeCN and de-ionised water 100 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent;

(ix) where an "ISOLUTE" column is referred to, this means a column containing 2 g of silica, the silica being contained in a 6 ml disposable syringe and supported by a porous disc of 54 Å pore size, obtained from International Sorbent Technology under the name "ISOLUTE"; "ISOLUTE" is a registered trade mark;

(x) the following abbreviations may be used hereinbefore or hereinafter:

| | |
|---|---|
| DCM | dichloromethane; |
| DMF | N,N-dimethylformamide; |
| TFA | trifluoroacetic acid; |
| TBTU | o-Benzotriazol-1-yl-N,N,N',N'-tetramethyluronium tetrafluoroborate; |
| EtOAc | ethyl acetate; and |
| MeCN | acetonitrile. |

Example 1

1,1-Dioxo-3(R)-3-butyl-3-ethyl-5-(R)-5-phenyl-8-[N-((R)-α-carboxybenzyl)carbamoylmethoxy]-2,3,4,5-tetrahydro-1,4-benzothiazepine and 1,1-Dioxo-3(S)-3-butyl-3-ethyl-5-(S)-5-phenyl-8-[N-((R)-α-carboxybenzyl)carbamoylmethoxy]-2,3,4,5-tetrahydro-1,4-benzothiazepine (+−)-trans-1,1-Dioxo-3-butyl-3-ethyl-5-phenyl-8-(carboxymethoxy)2,3,4,5-tetrahydro-1,4-benzothiazepine (Method 1; 13 mg, 0.03 mmol) methyl (2R)-amino(phenyl) acetate (7.5 mg, 0.037 mmol) and diisopropylethylamine (24 mg, 0.19 mmol) were dissolved in DCM (1.5 ml). The mixture was stirred for 10 min and then TBTU (12 mg, 0.037 mmol) was added and the reaction mixture was stirred for 30 min. The solvent was removed under reduced pressure. The residue was dissolved in ethanol (2 ml) and sodium hydroxide (2 mg) was added. The mixture was stirred for 30 min and the solvent was evaporated. The residue was purified by chromatography (DCM:EtOAc:AcOH, 100:10:3) giving the title compound (5.5 mg, 32%). M/z: 565.3 (MH$^+$), 563.2 (M$^-$).

Example 2

1,1-Dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine and 1,1-Dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine An equal mixture of 1,1-dioxo-3-(R)-3-butyl-3-ethyl-5-(R)-5-phenyl-8-(N-{(R)-α-[N-(t-butoxycarbonylmethyl)carbamoyl]benzyl}carbamoylmethoxy)-2,3,4,5-tetrahydro-1,4-benzothiazepine and 1,1-dioxo-3-(S)-3-butyl-3-ethyl-5-(S)-5-phenyl-8-(N-{(R)-α-[N-(t-butoxycarbonylmethyl)carbamoyl]benzyl}carbamoylmethoxy)-2,3,4,5-tetrahydro-1,4-benzothiazepine (Method 2; 27 mg, 0.040 mmol) were dissolved in 2 ml DCM. Trifluoroacetic acid (0.2 ml, 2.60 mmol) was added and the mixture was stirred overnight at ambient temperature. The reaction mixture was concentrated under reduced pressure and then purified with preparative HPLC using an MeCN/ammonium acetate buffer gradient (5/95 to 60/40) as eluent. The MeCN was evaporated and lyophilisation of the remaining solution resulted in the title products in 69% yield (16 mg). NMR (400 MHz, MeOD): 0.81 (t, 3H), 0.89 (t, 3H), 1.11–1.35 (m, 4H), 1.41–1.50 (m, 1H), 1.52–1.62 (m, 1H), 1.74–1.84 (m, 1H), 2.17–2.28 (m, 1H), 3.34 (ABq, 2H), 3.87 (ABq, 2H), 4.63–4.66 (m, 2H), 5.61 (s, 1H), 6.00 (s, 1H), 6.59–6.64 (m, 1H), 6.95–7.01 (m, 1H), 7.27–7.44 (m, 10H), 7.64–7.67 (m, 1H); m/z: 622 (M+1).

Example 3

3,5-trans-1,1-Dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-Dioxo-3-ethyl-3-butyl-5-phenyl-7-bromo-8-(carboxymethoxy)-2,3,4,5-tetrahydro-1,4-benzothiazepine (Method 5; 50 mg, 0.10 mmol) was dissolved in DCM (3 ml). Lutidine (0.023 ml, 0.198 mmol), TBTU (38 mg, 0.118 mmol) and (R)-α-[N-(t-butoxycarbonylmethyl)carbamoyl]benzylamine (Method 4; 44 mg, 0.167 mmol) were added successively. The mixture was stirred over night at ambient temperature. The solution was concentrated to 1 ml and TFA (1.3 ml) was added. The mixture was concentrated after 1.5 h and the residue was purified using preparative HPLC. A gradient from 40% to 60% of MeCN in 0.1 M ammonium acetate buffer was used as eluent. Lyophilisation yielded 39 mg (57%). NMR (400 MHz) 0.75 (t, 3H), 0.95 (t, 3H), 1.2–1.4 (m, 6H), 1.75–1.9 (m, 1H), 2.2–2.4 (m, 1H), 3.35 (dd, 2H), 3.85 (dd, 2H), 4.7–4.8 (m, 2H), 5.6 (s, 1H), 6.0 (d, 1H), 6.8 (d, 1H), 7.25–7.5 (m, 10H), 7.6 (d, 1H); m/z: 700 (M) and 702 (M+2)$^{2+}$.

Example 4

3,5-trans-1,1-Dioxo-3-(S)-3-ethyl-3-butyl-4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-Dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-Dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine (Example 3; 14 mg, 0.02 mmol) was dissolved in 2 ml DCM. m-Chloroperoxybenzoic acid (5.5 mg, 0.022 mmol) was added and the mixture was stirred for 30 min. The diastereomers of the title compound were separated using preparative HPLC on a C8 column. A gradient from 30% to 60% of MeCN in 0.1 M ammonium acetate buffer was used as eluent. The two compounds were lyophilized and the first eluting diastereomer was obtained in 5.4 mg and the second in 4.9 mg. M/z: 716 (M) and 718 (M+2)$^{2+}$. NMR (400 MHz) (diastereomer 1) 0.86 (t, 3H), 0.95 (t, 3H), 1.1–1.4 (m, 3H), 1.4–1.55 (m, 2H), 1.68–1.8 (m, 1H), 2.0–2.2 (m, 2H), 3.4 (dd, 2H), 3.88 (Abq, 2H), 4.76 (Abq, 2H), 5.6 (s, 1H), 6.45 (s, 1H), 6.88 (s, 1H), 7.25–7.50 (m, 10H), 7.56 (s, 1H). NMR (diastereomer 2) (400 MHz) 0.87 (t, 3H), 0.95 (t, 3H), 1.1–1.4 (m, 3H), 1.4–1.55 (m, 2H), 1.68–1.8 (m, 1H), 2.0–2.22 (m, 2H), 3.4 (dd, 2H), 3.82 (Abq, 2H), 4.76 (Abq, 2H), 5.6 (s, 1H), 6.46 (s, 1H), 6.88 (s, 1H), 7.25–7.50 (m, 10H), 7.57 (s, 1H).

Example 5

3,5-trans-1,1-Dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine 3,5-trans-1,1-Dioxo-3-ethyl-3-butyl-5-phenyl-7-methylthio-8-(carboxymethoxy)-2,3,4,5-tetrahydro-1,4-benzothiazepine (Method 6; 50 mg, 0.105 mmol) was dissolved in DCM (2 ml). 2,6-Lutidine (0.025 ml, 0.215 mmol), TBTU (45 mg, 0.140 mmol) and R)-α-[N-(t-butoxycarbonylmethyl)carbamoyl]benzylamine (Method 4; 43 mg, 0.163 mmol) were added successively. The mixture was stirred for 2 hours at ambient temperature. The solution was concentrated and the intermediate ester was purified by chromatography on silica using DCM/EtOAc (9/1) as eluent. The solvent was evaporated to yield 45 mg (60%). M/z: 724. The ester was dissolved in 3 ml DCM and hydrolysed by addition of TFA (1 ml). After 2 hours the mixture was concentrated and purified using preparative HPLC. A gradient of MeCN from 40% to 60% in 0.1 M ammonium acetate buffer was used as eluent. Lyophilisation yielded 33 mg (80%). NMR (400 MHz): 0.75–0.85 (m, 3H), 0.85–0.95 (m, 3H), 1.1–1.65 (m, 6H), 1.75–1.9 (m, 1H), 2.0 (s, 3H), 2.2–2.4 (m, 1H), 3.1–3.55 (m, 2H), 3.85 (ABq, 2H), 4.6–4.8 (m, 2H), 5.6 (s, 1H), 5.98–6.03 (m, 1H), 6.4 (s, 1H), 7.25–7.56 (m, 11H); m/z: 668.

Example 6

3,5-trans-1,1-Dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt 3,5-trans-1,1-Dioxo-3-ethyl-3-butyl-5-phenyl-7-methylthio-8-(carboxymethoxy)-2,3,4,5-tetrahydro-1,4-benzothiazepine (Method 6; 33 mg, 0.070 mmol) was dissolved in DMF (3 ml). 2-{[(2R)-2-Amino-2-(4-hydroxyphenyl)ethanoyl]amino}ethanesulphonic acid Method 8; 23 mg, 0.084 mmol), N-methylmorpholine (0.025 ml, 0.227 mmol) and TBTU (27 mg, 0.084 mmol) were added successively and the mixture was stirred overnight. The solvent was removed and the crude product was purified using preparative HPLC. A gradient from 40% to 70% of MeCN in 0.1 M ammonium acetate buffer was used as eluent. Lyophilisation yielded 42 mg (80%) of the ammonium salt. NMR(400 MHz): 0.73–0.85 (m, 3H), 0.85–0.98 (m, 3H), 1.1–1.7 (m, 6H), 1.75–1.9 (m, 1H), 2.0 (s, 3H), 2.15–2.4 (m, 1H) 2.85–3.0 (m, 2H), 3.1–3.55 (m, 2H), 3.5–3.65 (m, 2H), 4.6–4.8 (m, 2H), 5.35–5.39 (m, 1H), 5.98–6.05 (m, 1H), 6.4 (s, 1H), 6.75 (d, 2H), 7.15–7.5 (m, 8H); m/z: 734.

Example 7

1,1-Dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt 1,1-Dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt The diasteromeric mixture of 3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4benzothiazepine (Example 5; 17 mg, 0.026 mmol) was separated by chiral chromatography on a Chirobiotic V chiral stationary phase. Two columns (250×20 mm) in series were used. A mobile phase consisting of 80% MeOH in water with 0.1% Et₃N and 0.1% HOAc was used as eluent. The first eluting diastereomer was collected in a 50 ml fraction and the solvent was removed under reduce pressure. Et₃N remained according to NMR-analysis and the diastereomer was purified by chromatography over 0.5 g SiO₂ using DCM/MeOH (9/1) as eluent. The solvent was removed and the product was dissolved in water and some MeCN. Lyophilisation yielded a white solid, which was dissolved in MeOH and filtered. A second lyophilisation yielded the diastereomer as the Et₃N salt in 1 mg (4%). M/z: 668. NMR (HOAc-d4) was consistent with Example 5. The e.e. was determined as 99%. The second eluting diastereomer was collected in a 200 ml fraction and the solvent was removed under reduced pressure. The residue was purified using preparative HPLC on a C8 column. A gradient from 35% to 50% MeCN in 0.1 M ammonium acetate was used as eluent. Lyophilisation yielded the diastereomer as the Et₃N salt in 3 mg (17 mg). M/z: 668. The e.e. was determined as 97%.

Preparation of Starting Materials

The starting materials for the Examples above are either commercially available or are readily prepared by standard Methods from known materials. For Example, the following reactions are an illustration, but not a limitation, of some of the starting materials used in the above reactions.

Method 1

(+−)-trans-1,1-Dioxo-3-butyl-3-ethyl-5-phenyl-8-(carboxymethoxy)-2,3,4,5-tetrahydro-1,4-benzothiazepine 1,1-Dioxo-3-butyl-3-ethyl-5-phenyl-8-hydroxy-2,3,4,5-tetrahydro-1,4benzothiazepine (prepared according to WO/9605188; 83 mg, 0,22 mmol), ethyl bromoacetate (55 mg, 0.33 mmol) and sodium carbonate (70 mg, 0.66 mmol) in acetonitrile (3 ml) were warmed to reflux for 40 hours. The solvent was removed under reduced pressure and the crude product was dissolved in ethanol (4 ml). Sodium hydroxide (0.1 g) was added and the mixture was warmed to reflux for 1 hour. The solvent was removed under reduced pressure and the residue was partitioned between DCM and 2 M acetic acid. The organic layer was dried over sodium sulphate and the solvent was removed under reduced pressure. The residue was purified by chromatography (EtOAc: formic acid, 500:1) to give 61 mg (64%) of the title compound. NMR (500 MHz, CDCl₃): 0.86 (t, 3H), 0.92 (t, 3H), 1.0–1.05 (m, 1H), 1.2–1.4 (m, 3H), 1.6–1.75 (m, 2H), 1.85–1.95 (m, 1H), 2.38–2.47 (m, 1H), 3.45 (s, 2H), 4.5 (s, 2H), 6.17 (s, 1H), 6.75 (d, 1H), 6.86 (dd, 1H), 7.37–7.5 (m, 5H), 7.64 (d, 1H).

Method 2

1,1-Dioxo-3(R)-3-butyl-3-ethyl-5-(R)-5phenyl-8-(N-{(R)-α-[N-(t-butoxycarbonylmethyl)carbamoyl]benzyl}carbamoylmethoxy)-2,3,4,5-tetrahydro-1,4-benzothiazepine; and 1,1-Dioxo-3(S)-3-butyl-3-ethyl-5-(S)-5-phenyl-8-(N-{(R)-α-[N-(t-butoxycarbonylmethyl)carbamoyl]benzyl}carbamoylmethoxy)-2,3,4,5-tetrahydro-1,4-benzothiazepine (+−)-trans-1,1-Dioxo-3-butyl-3-ethyl-5-phenyl-8-(carboxymethoxy)-2,3,4,5-tetrahydro-1,4-benzothiazepine (Method 1; 17.5 mg, 0.041 mmol) was dissolved in DCM (3 ml). 2,6-Lutidine (0.010 ml, 0.086 mmol), TBTU (16.4 mg, 0.051 mmol) and (R)-α-[N-(t-butoxycarbonylmethyl)carbamoyl]benzylamine (Method 4; 16.3 mg, 0.062 mmol) were added successively. The mixture was stirred for 1 hour at ambient temperature. The solution was concentrated and the crude product was purified by chromatography on silica using DCM/EtOAc (8/2) as eluent. The solvent was evaporated and the title products were obtained in 98% yield (27 mg). M/z: 678 (M+1).

Method 3

(R)-N-Benzyloxycarbonyl-α-[N-(t-butoxycarbonylmethyl)carbamoyl]benzylamine (2R)-{[(Benzyloxy)carbonyl]amino}(phenyl)acetic acid (10 g, 35.0 mmol) and t-butylglycine hydrochloride (6.3 g, 37.4 mmol) were dissolved in DCM (200 ml) with 2,6-lutidine (8.2 ml, 70.4 mmol). After stirring 5 min at 0° C. TBTU (12.4 g, 38.6 mmol) was added and stirring was continued for 1.5 hours at 0° C. and 3.75 hours at room temperature. The reaction mixture was washed with water (2×100 ml), dried (MgSO$_4$) and purified with flash chromatography (DCM:EtOAc 7:1→5:1) to give the title compound (13 g, 94%). NMR (500 MHz, CDCl$_3$): 1.45 (s, 9H), 3.84 (d, 1H), 4.00 (dd, 1H), 5.10 (m, 2H), 5.28 (brs, 1H), 6.13 (brs, 1H), 6.23 (brs, 1H), 7.30–7.44 (m, 10H).

Method 4

(R)-α-[N-(t-Butoxycarbonylmethyl)carbamoyl]benzylamine (R)-N-Benzyloxycarbonyl-α-[N-(t-butoxycarbonylmethylcarbamoyl]benzylamine (Method 3; 12.8 g, 32.2 mmol) was dissolved in EtOH (99%, 200 ml) and toluene (50 ml). Pd/C (10%, 0.65 g) was added and hydrogenation was performed at atmospheric pressure for 5.5 hours at room temperature. The reaction mixture was filtered through diatomaceous earth and the solvents were evaporated to give the title compound (8.4 g, 99%). NMR (600 MHz, CDCl$_3$): 1.45 (s, 9H), 3.93 (m, 2H), 4.54 (s, 1H), 7.31–7.42 (m, 5H), 7.51 (brs, 1H).

Method 5

3,5-trans-1,1-Dioxo-3-ethyl-3-butyl-5-phenyl-7-bromo-8-(carboxymethoxy-2,3,4,5-tetrahydro-1,4-benzothiazepine The title compound was prepared as described in Method 6 starting from (+/−)-trans-7-bromo-3-butyl-3-ethyl-2,3,4,5-tetrahydro-5-phenyl-1,4-benzothiazepin-8-ol 1,1-dioxide (WO96/05188; 81 mg, 0.18 mmol). The intermediate ethyl ester was obtained in 94% yield (m/z: 538(M) and 540(M+2)). The product was obtained in 50 mg (58%). NMR 0.75 (t, 3H), 0.95 (t, 3H), 1.2–1.45 (m, 6H), 1.75–1.9 (m, 1H), 2.2–2.4 (m, 1H), 3.35 (dd, 2H), 4.8 (s, 2H), 6.0 (s, 1H), 6.8 (s, 1H), 7.3–7.5 (m, 5H), 7.55 (s, 1H); m/z: 510 (M) and 512 (M+2)$^{2+}$.

Method 6

3,5-trans-1,1-Dioxo-3-ethyl-3-butyl-5-phenyl-7-methylthio-8-(carboxymethoxy)-2,3,4,5-tetrahydro-1,4-benzothiazepine The title compound was prepared from 3,5-trans-1,1-dioxo-3-ethyl-3-butyl-5-phenyl-7-methylthio-8-hydroxy-2,3,4,5-tetrahydro-1,4-benzothiazepine (Method 7; 153 mg, 0.36 mmol) using the procedure described in Method 1. The intermediate ethyl ester was extracted between diluted HCl and DCM. The DCM phase was washed with brine, dried with Na$_2$SO$_4$ and concentrated. M/z 506. The crude product was dissolved in THF/H$_2$O (3/1; 4 ml) and LiOH (22 mg, 0.91 mmol) was added. The mixture was stirred for 2 h and the solvent was removed under reduced pressure. The crude product was purified using preparative HPLC. A gradient from 40% to 60% MeCN in 0.1 M ammonium acetate buffer was used as eluent. The MeCN was removed under reduced pressure and the remaining aqueous solution was acidified using 5% HCl and was then extracted with DCM. The DCM layer was dried with Na$_2$SO$_4$ and concentrated. The crude product was co-evaporated with diethyl ether. The obtained crystals were filtered off and dried. Mass: 158 mg (91%). NMR 0.75 (t, 3H), 0.9 (t, 3H), 1.1–1.7 (m, 6H), 1.7–1.9 (m, 1H), 2.0 (s, 3H), 2.2–2.4 (m,1H), 3.3 (dd, 2H), 4.75 (s, 2H) 6.0 (s, 1H), 6.4 (s, 1H), 7.3–7.5 (m, 6H); m/z: 478.

Method 7

3,5-trans-1,1-Dioxo-3-ethyl-3-butyl-5-phenyl-7-methylthio-8-hydroxy-2,3,4,5-tetrahydro-1,4-benzothiazepine (+/−)-trans-7-Bromo-3-butyl-3-ethyl-2,3,4,5-tetrahydro-8-methoxy-5-phenyl-1,4-benzothiazepine 1,1-dioxide (prepared according to WO 96/05188; 300 mg, 0.64 mmol) was dissolved in 5 ml DMF under N$_2$(g)-atmosphere. Sodium thiomethylate (150 mg, 2.14 mmol) was added and the mixture was heated to 110° C. for 2 h. The solvent was removed under reduced pressure and the residue was extracted between 5% HCl and EtOAc. The organic phase was washed with brine, dried with Na$_2$SO$_4$ and concentrated. The product was purified using preparative HPLC. A gradient from 40% to 100% of MeCN in 0.1 M ammonium acetate buffer was used as eluent. Lyophilisation yielded 153 mg, 57%. M/z: 420.

Method 8

2-{[(2R)-2-Amino-2-(4-hydroxyphenyl)ethanoyl]amino}ethanesulphonic acid

N-Boc-(D)-4hydroxyphenylglycine (1.00 g, 3.21 mmol) was dissolved in DMF (5 ml) and tetrabutylammonium taurine (2.36 g, 6.42 mmol) was added together with additional DMF (5 ml). The resulting suspension was cooled on ice and TBTU (1.24 g, 3.85 mmol) was added. The ice bath was removed after 30 min and the mixture was stirred for 2 hours before it was filtered and concentrated. TFA in DCM (20%, 20 ml) was added and the reaction mixture was stirred over night. Ethanol (20 ml) was added and the solvents evaporated. The crude product was refluxed in ethanol (100 ml) for 1 hour. Filtration yielded the pure title compound as a white solid, 626 mg (71%). NMR (DMSO-d$_6$): 2.4–2.6 (m, 2H), 3.2–3.4 (m, 2H), 4.79 (s, 1H), 6.78 (d, 2H),7.23 (d, 2H), 8.22 (t, 1H), 8.4 (brs, 3H), 9.7 (s, 1H).

What is claimed is:

1. A compound of formula (I):

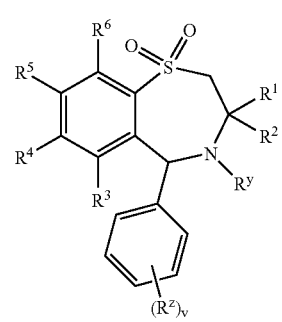

wherein:
One of R$^1$ and R$^2$ are selected from hydrogen, C$_{1-6}$alkyl or C$_{2-6}$alkenyl and the other is selected from C$_{1-6}$alkyl or C$_{2-6}$alkenyl;

R$^y$ is selected from hydrogen, hydroxy, C$_{1-6}$alkyl, C$_{1-4}$alkoxy and C$_{1-6}$alkanoyloxy;

R$^z$ is selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl;

v is 0–5;

one of R$^4$ and R$^5$ is a group of formula (IA):

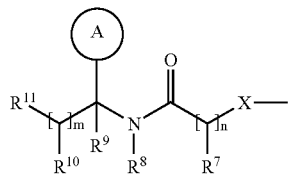

(IA)

R$^3$ and R$^6$ and the other of R$^4$ and R$^5$ are independently selected from hydrogen, halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R$^3$ and R$^6$ and the other of R$^4$ and R$^5$ may be optionally substituted on carbon by one or more R$^{16}$;

X is —O—, —N(R$^a$)—, —S(O)$_b$— or —CH(R$^a$)—; wherein R$^a$ is hydrogen or C$_{1-6}$alkyl and b is 0–2;

Ring A is aryl or heteroaryl; wherein Ring A is optionally substituted by one or more substituents selected from R$^{17}$;

R$^7$ is hydrogen, C$_{1-4}$alkyl, carbocyclyl or heterocyclyl; wherein R$^7$ is optionally substituted by one or more substituents selected from R$^{18}$;

R$^8$ is hydrogen or C$_{1-4}$alkyl;

R$^9$ is hydrogen or C$_{1-4}$alkyl;

R$^{10}$ is hydrogen, C$_{1-4}$alkyl, carbocyclyl or heterocyclyl; wherein R$^{10}$ is optionally substituted by one or more substituents selected from R$^{19}$;

R$^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from C$_{1-6}$alkyl; or R$^{11}$ is a group of formula (IB):

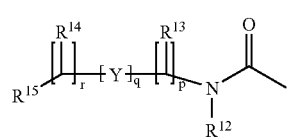

(IB)

wherein:

Y is —N(R$^x$)—, —N(R$^x$)C(O)—, —O—, and —S(O)a-; wherein a is 0–2 and R$^x$ is hydrogen or C$_{1-4}$alkyl;

R$^{12}$ is hydrogen or C$_{1-4}$alkyl;

R$^{13}$ and R$^{14}$ are independently selected from hydrogen, C$_{1-6}$alkyl, carbocyclyl or heterocyclyl; wherein R$^{13}$ and R$^{14}$ may be independently optionally substituted by one or more substituents selected from R$^{20}$;

R$^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from C$_{1-6}$alkyl; or R$^{15}$ is a group of formula (IC):

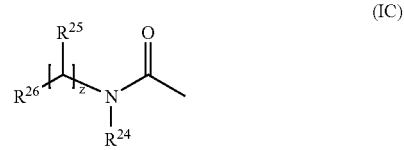

(IC)

wherein:

R$^{24}$ is selected from hydrogen or C$_{1-4}$alkyl;

R$^{25}$ is selected from hydrogen, C$_{1-4}$alkyl, carbocyclyl, heterocyclyl or R$^{27}$; wherein said C$_{1-4}$alkyl, carbocyclyl or heterocyclyl may be independently optionally substituted by one or more substituents selected from R$^{28}$;

R$^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from C$_{1-6}$alkyl;

p is 1–3; wherein the values of R$^{13}$ may be the same or different;

q is 0–1;

r is 0–3; wherein the values of R$^{14}$ may be the same or different;

m is 0–2; wherein the values of R$^{10}$ may be the same or different;

n is 1–3; wherein the values of R$^7$ may be the same or different;

z is 0–3; wherein the values of R$^{25}$ may be the same or different;

R$^{16}$, R$^{17}$ and R$^{18}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R$^{16}$, R$^{17}$ and R$^{18}$ may be independently optionally substituted on carbon by one or more R$^{21}$;

or a pharmaceutically acceptable salt, or an in vivo hydrolysable ester formed on an available carboxy or hydroxy thereof, or an in vivo hydrolysable amide formed on an available carboxy thereof.

2. A compound of formula (I) as claimed in claim 1 wherein one of R$^1$ and R$^2$ is ethyl and the other is butyl or a pharmaceutically acceptable salt, or an in vivo hydrolysable ester formed on an available carboxy or hydroxy thereof, or an in vivo hydrolysable amide formed on an available carboxy thereof.

3. A compound of formula (I) as claimed in claim 1 wherein R$^y$ is hydrogen or hydroxy or a pharmaceutically acceptable salt, or an in vivo hydrolysable ester formed on an available carboxy or hydroxy thereof, or an in vivo hydrolysable amide formed on an available carboxy thereof.

4. A compound of formula (I) as claimed in claim 1 wherein v is 0 or a pharmaceutically acceptable salt, or an in vivo hydrolysable ester formed on an available carboxy or hydroxy thereof, or an in vivo hydrolysable amide formed on an available carboxy thereof.

5. A compound of formula (I) as claimed in claim 1 wherein R$^3$ and R$^6$ are hydrogen or a pharmaceutically acceptable salt, or an in vivo hydrolysable ester formed on an available carboxy or hydroxy thereof, or an in vivo hydrolysable amide formed on an available carboxy thereof.

6. A compound of formula (I) as claimed in claim 1 wherein $R^4$ is hydrogen, halo or $C_{1-4}$alkylS(O)$_a$ wherein a is 0 or a pharmaceutically acceptable salt, or an in vivo hydrolysable ester formed on an available carboxy or hydroxy thereof, or an in vivo hydrolysable amide formed on an available carboxy thereof.

7. A compound of formula (I) as claimed in claim 1 wherein $R^5$ is a group of formula (IA) (as depicted in claim 1);
wherein
X is —O—;
Ring A is phenyl or 4-hydroxyphenyl;
$R^7$ is hydrogen;
$R^8$ is hydrogen;
$R^9$ is hydrogen;
$R^{11}$ is carboxy; or $R^{11}$ is a group of formula (IB) (as depicted above); wherein
$R^{12}$ is hydrogen;
$R^{13}$ hydrogen;
$R^{15}$ is carboxy or sulpho;
p is 1 or 2;
q is 0;
r is 0;
m is 0; and
n is 1;
or a pharmaceutically acceptable salt, or an in vivo hydrolysable ester formed on an available carboxy or hydroxy thereof, or an in vivo hydrolysable amide formed on an available carboxy thereof.

8. A compound of formula (I) as claimed in claim 1 wherein
$R^1$ and $R^2$ are $C_{1-4}$alkyl;
v is 0;
$R^y$ is hydrogen or hydroxy;
$R^3$ and $R^6$ are hydrogen;
$R^4$ is hydrogen, halo or $C_{1-4}$alkylS(O)$_a$ wherein a is 0;
$R^5$ is a group of formula (IA) (as depicted above); wherein
X is —O—;
Ring A is aryl; wherein Ring A is optionally substituted by one or more substituents selected from $R^{17}$;
$R^7$ is hydrogen;
$R^8$ is hydrogen;
$R^9$ hydrogen;
$R^{11}$ is carboxy; or $R^{11}$ is a group of formula (IB) (as depicted above); wherein
$R^{12}$ hydrogen;
$R^{13}$ hydrogen;
$R^{15}$ is carboxy or sulpho;
p is 1 or 2;
q is 0;
r is 0;
m is 0;
n is 1; and
$R^{17}$ is hydroxy;
or a pharmaceutically acceptable salt, or an in vivo hydrolysable ester formed on an available carboxy or hydroxy thereof, or an in vivo hydrolysable amide formed on an available carboxy thereof.

9. A compound of formula (I) as claimed in claim 1 selected from
1,1-dioxo-3(R)-3-butyl-3-ethyl-5-(R)-5-phenyl-8-[N-((R)-α-carboxybenzyl) carbamoylmethoxy]-2,3,4,5-tetrahydro-1,4-benzothiazepine;

1,1-dioxo-3(S)-3-butyl-3-ethyl-5-(S)-5-phenyl-8-[N-((R)-α-carboxybenzyl) carbamoylmethoxy]-2,3,4,5-tetrahydro-1,4-benzothiazepine;
1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;
1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;
3,5-trans-1,1-dioxo-3-ethyl-3-butyl-5-phenyl-7-bromo-8-(N-{(R)-α-[N-(carboxymethyl)carbamoyl]benzyl}carbamoylmethoxy)-2,3,4,5-tetrahydro-1,4-benzothiazepine;
3,5-trans-1,1-dioxo-3-(S)-3-ethyl-3-butyl-4-hydroxy-5-(S)-5-phenyl-7-bromo-8-(N-{(R)-α-N-(carboxymethyl)carbamoyl]benzyl}carbamoylmethoxy)-2,3,4,5-tetrahydro-1,4-benzothiazepine
3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;
3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;
3,5-trans-1,1-dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt;
1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and
1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, or an in vivo hydrolysable ester formed on an available carboxy or hydroxy thereof, or an in vivo hydrolysable amide formed on an available carboxy thereof.

10. A process for preparing a compound of formula (I) or a pharmaceutically acceptable salt, or an in vivo hydrolysable ester formed on an available carboxy or hydroxy thereof, or an in vivo hydrolysable amide formed on an available carboxy thereof, as claimed in claim 1, which process comprises of:
Process 1): oxidising a benzothiazepine of formula (II):

(II)

Process 2): for compounds of formula (I) wherein X is
—O—, —NR$^a$ or —S—; reacting a compound of
formula (IIIa) or (IIIb):

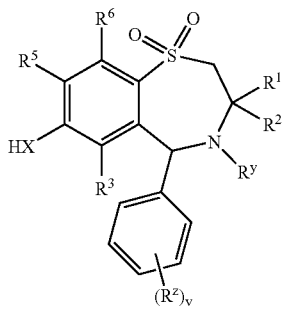
(IIIa)

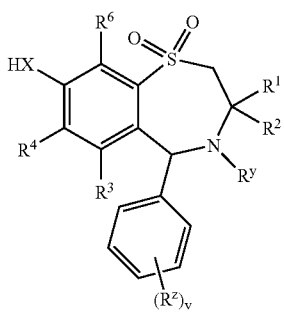
(IIIb)

with a compound of formula (IV):

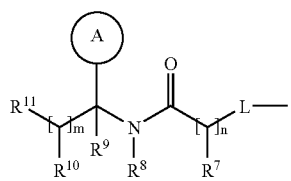
(IV)

wherein L is a displaceable group;

Process 3): reacting an acid of formula (Va) or (Vb):

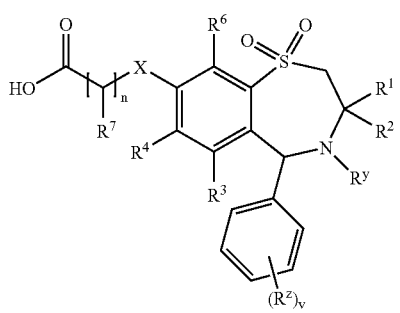
(Va)

-continued

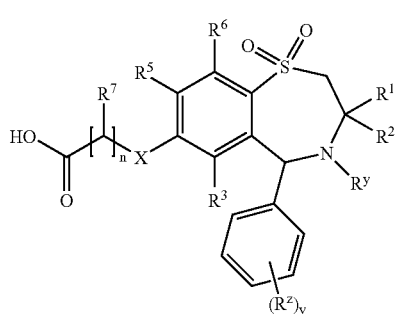
(Vb)

or an activated derivative thereof; with an amine of
formula (VI):

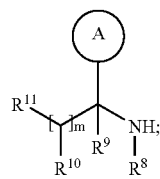
(VI)

Process 4): for compounds of formula (I) wherein R$^{11}$ is
a group of formula (IB); reacting a compound of
formula (I) wherein R$^{11}$ is carboxy with an amine of
formula (VII):

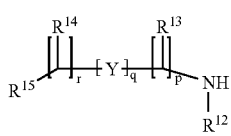
(VII)

Process 5): for compounds of formula (I) wherein R$^{11}$ is
a group of formula (IB) and R$^{15}$ is a group of formula
(IC) reacting a compound of formula (I) wherein R$^{15}$ is
carboxy with an amine of formula (VIII):

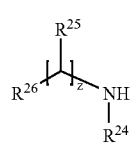
(VIII)

Process 6) for compounds of formula (I) wherein one of
R$^4$ and R$^5$ are independently selected from C$^{1-6}$alky-
lthio optionally substituted on carbon by one or more
R$^{16}$; reacting a compound of formula (IXa) or (IXb):

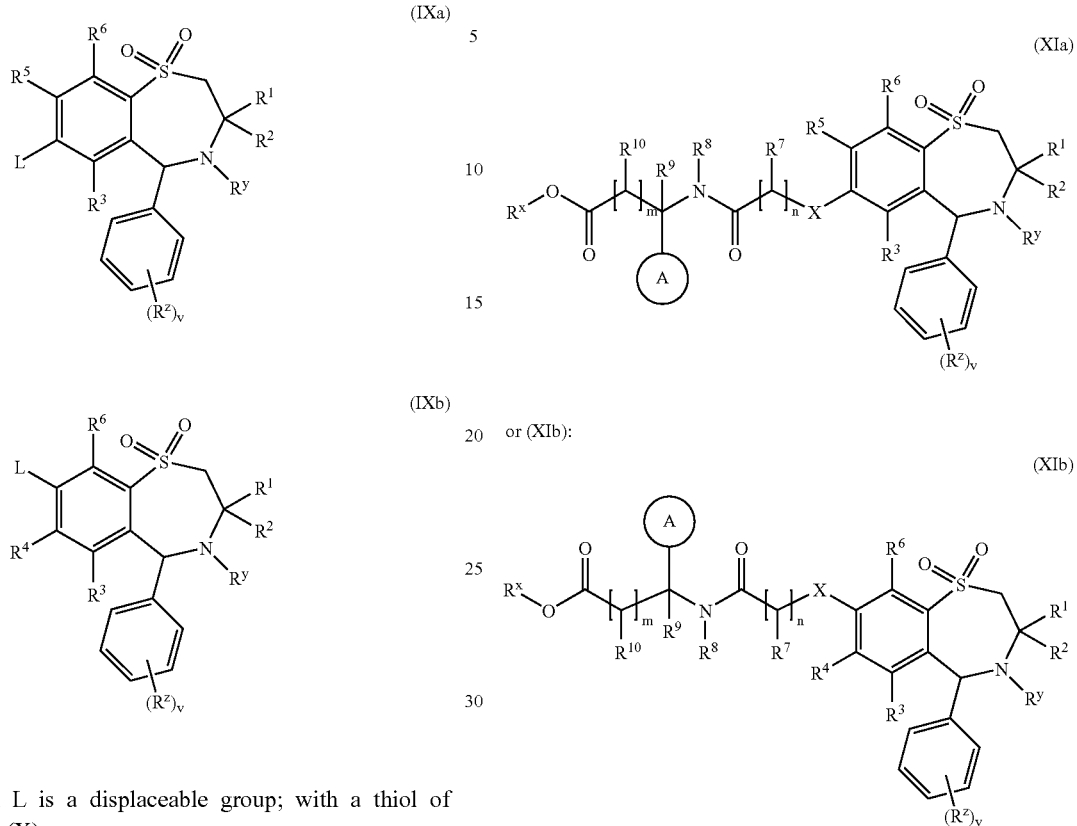

wherein L is a displaceable group; with a thiol of formula (X):

R$^m$—H (X)

wherein R$^m$ is C$^{1-6}$alkylthio optionally substituted on carbon by one or more R$^{16}$;

Process 7): for compounds of formula (I) wherein R$^{11}$ is carboxy; deprotecting a compound of formula (XIa):

or (XIb):

wherein R$^x$ together with the —OC(O)— group to which it is attached forms an ester;

Process 8): for compounds of formula (I) wherein R$^{11}$ is a group of formula (IB) and R$^{15}$ is carboxy; deprotecting a compound of formula (XIIa):

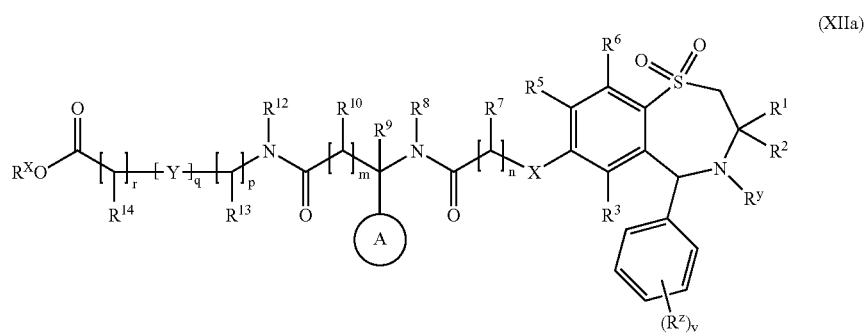

or (XIIb):

-continued (XIIb)

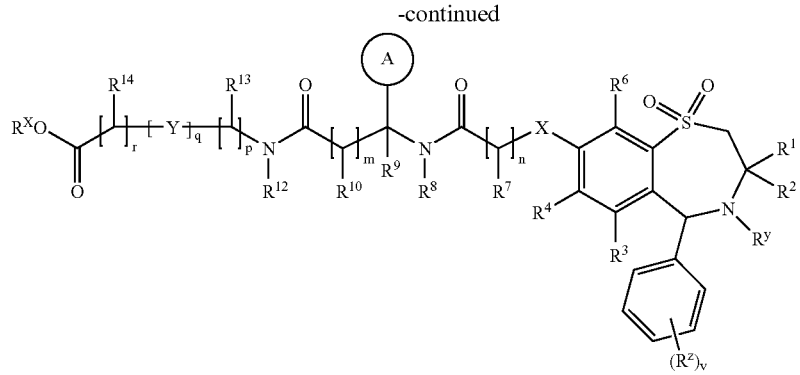

wherein $R^x$ together with the —OC(O)— group to which it is attached forms an ester;

Process 9): for compounds of formula (I) wherein $R^{11}$ is a group of formula (IB) and Y is —N($R^x$)C(O)—; reacting an acid of formula (XIIIa):

(XIIIa)

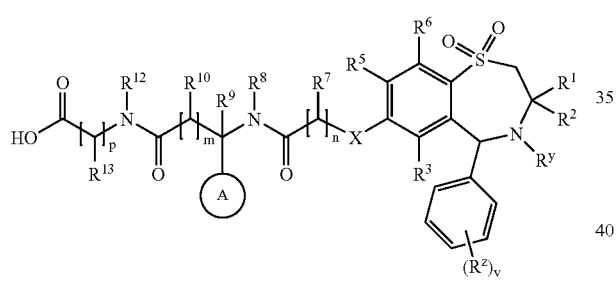

or (XIIIb):

-continued (XIIIb)

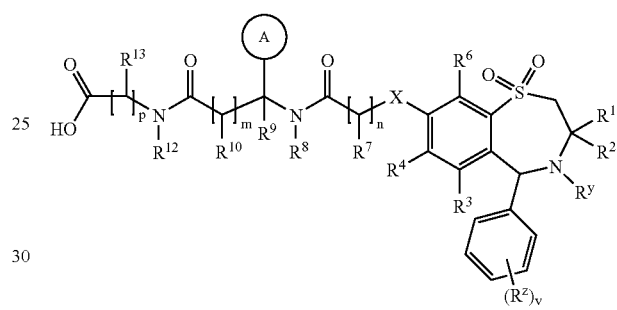

or an activated derivative thereof; with an amine of formula (XIV):

(XIV)

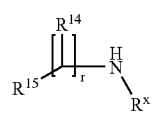

or Process 10): for compounds of formula (I) wherein $R^{11}$ is a group of formula (IB), $R^{15}$ is a group of formula (IC) and $R^{26}$ is carboxy; deprotecting a compound of formula (XVa):

(XVa)

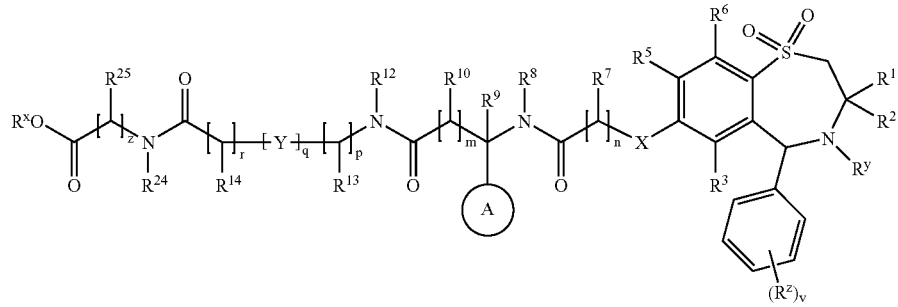

or (XVb):

-continued (XVb)

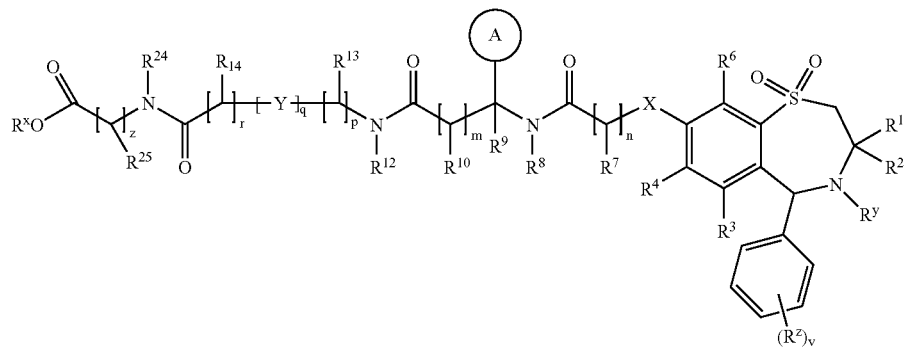

wherein R$^x$ together with the —OC(O)— group to which it is attached forms an ester; and thereafter optionally:
i) converting a compound of the formula (I) into another compound of the formula (I);
ii) removing any protecting groups;
iii) forming a pharmaceutically acceptable salt, or forming an in vivo hydrolysable ester on an available carboxy or hydroxy thereof, or forming an in vivo hydrolysable amide formed on an available carboxy.

11. A pharmaceutical composition which comprises a compound of formula (I), or a pharmaceutically acceptable salt, or an in vivo hydrolysable ester formed on an available carboxy or hydroxy thereof, or an in vivo hydrolysable amide formed on an available carboxy thereof, as claimed in any one of claims 1 to 9, in association with a pharmaceutically-acceptable diluent or carrier.

* * * * *